United States Patent
Sakai et al.

(10) Patent No.: US 9,766,447 B2
(45) Date of Patent: Sep. 19, 2017

(54) LIGHT SOURCE APPARATUS

(71) Applicant: OLYMPUS CORPORATION, Tokyo (JP)

(72) Inventors: Aiko Sakai, Kodaira (JP); Ryo Machida, Kanagawa (JP); Yusuke Yabe, Chofu (JP); Tomoya Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/196,756

(22) Filed: Jun. 29, 2016

(65) Prior Publication Data

US 2016/0306163 A1 Oct. 20, 2016

Related U.S. Application Data

(63) Continuation of application No. PCT/JP2015/059325, filed on Mar. 26, 2015.

(30) Foreign Application Priority Data

Apr. 17, 2014 (JP) ................................. 2014-085818

(51) Int. Cl.
*H05B 33/08* (2006.01)
*G02B 27/14* (2006.01)
(Continued)

(52) U.S. Cl.
CPC ........ *G02B 23/2461* (2013.01); *A61B 1/0638* (2013.01); *A61B 1/0684* (2013.01);
(Continued)

(58) Field of Classification Search
CPC . A61B 1/0638; A61B 1/0669; A61B 1/00009; A61B 1/07; A61B 1/00165;
(Continued)

(56) References Cited

U.S. PATENT DOCUMENTS

| 2005/0242298 A1* | 11/2005 | Genet | ................... | A61B 5/0068 250/461.2 |
| 2011/0279494 A1* | 11/2011 | Drumm | ................ | H04N 9/3129 345/697 |

(Continued)

FOREIGN PATENT DOCUMENTS

| JP | 2005-259704 A | 9/2005 |
| JP | 2009-513011 A | 3/2009 |

(Continued)

OTHER PUBLICATIONS

International Search Report dated Jun. 16, 2015 issued in PCT/JP2015/059325.

(Continued)

*Primary Examiner* — Alexander H Taningco
*Assistant Examiner* — Renan Luque
(74) *Attorney, Agent, or Firm* — Scully, Scott, Murphy & Presser, P.C.

(57) ABSTRACT

A light source apparatus includes first and second light sources having different maximum light amounts used, a first light amount detection section detecting a light amount of first light of the first light source, a second light amount detection section detecting a light amount of second light of the second light source, a light amount limiting section limiting a light amount of light incident upon the second light amount detection section so that light amounts detected in the first light amount detection section and the second light amount detection section match a predetermined value within a detection range when light with the maximum light amounts used are emitted from the first light source and the second light source, and a control section controlling amounts of light emission of the first light source and the second light source based on detection results of the first and second light amount detection sections.

9 Claims, 5 Drawing Sheets

(51) Int. Cl.
*A61B 1/06* (2006.01)
*A61B 1/07* (2006.01)
*G02B 23/24* (2006.01)
*G01J 1/04* (2006.01)

(52) U.S. Cl.
CPC .............. *A61B 1/07* (2013.01); *G01J 1/0418* (2013.01); *G01J 1/0425* (2013.01); *G01J 1/0437* (2013.01); *G01J 1/0488* (2013.01); *G02B 23/2469* (2013.01); *G02B 27/141* (2013.01); *H05B 33/0803* (2013.01); *H05B 33/0848* (2013.01); *H05B 33/0869* (2013.01)

(58) Field of Classification Search
CPC . A61B 1/0684; A61B 1/00172; A61B 5/0071; A61B 5/0084; A61B 1/045; A61B 1/0646; A61B 1/00096; A61B 1/00045; H05B 33/0869; H05B 33/0872; H05B 33/0863; H05B 33/086; H05B 33/0818; H05B 33/0866; H05B 37/02; G02B 23/26; G02B 21/0028; G02B 21/0032; G02B 21/0048; G02B 21/0072; G02B 21/0076; G02B 21/0084; G02B 23/2415; G02B 23/2423; G02B 23/2453; G02B 23/2469
USPC ....... 315/151, 119, 149, 159, 224, 307, 308, 315/312, 360; 345/207, 83, 697; 600/178, 476, 109, 160, 182, 473, 478, 600/177, 181, 101, 103, 111, 118, 129, 600/175, 179, 180, 317, 339; 250/216, 250/226, 458.1, 201.1, 205, 372, 201.3, 250/208.1, 330, 338.1, 461.2, 484.4
See application file for complete search history.

(56) References Cited

U.S. PATENT DOCUMENTS

2012/0105403 A1* 5/2012 Huang ................ G06F 3/03545
345/207
2013/0003054 A1* 1/2013 Kamimura ................ G01J 3/02
356/300
2013/0345517 A1 12/2013 Morimoto et al.

FOREIGN PATENT DOCUMENTS

JP          2009-192772 A    8/2009
JP             2014-301 A    1/2014
JP           2015-85097 A    5/2015

OTHER PUBLICATIONS

Japanese Office Action dated Dec. 1, 2015 issued in JP 2015-541358.

* cited by examiner

US 9,766,447 B2

LIGHT SOURCE APPARATUS

CROSS REFERENCE TO RELATED APPLICATION

This application is a continuation application of PCT/JP2015/059325 filed on Mar. 26, 2015 and claims benefit of Japanese Application No. 2014-085818 filed in Japan on Apr. 17, 2014, the entire contents of which are incorporated herein by this reference.

BACKGROUND OF INVENTION

1. Field of the Invention

The present invention relates to a light source apparatus suitable for use in an endoscope.

2. Description of the Related Art

Conventionally, endoscopes are widely used in which an elongated endoscope is inserted into a body cavity or the like to observe a region to be inspected or perform various kinds of treatment. In such endoscopes, a light source apparatus for photographing an interior of the cavity is adopted. In recent years, light source apparatuses may be used which adopt a semiconductor light source such as an LED as a light-emitting section. Such light source apparatuses can perform light adjustment control of the LED through PWM control that changes a duty ratio of drive pulses and current control that changes an LED current.

As an illumination apparatus using such an LED light source, there is an apparatus disclosed in Japanese Patent Application Laid-Open Publication No. 2009-192772. The apparatus according to Japanese Patent Application Laid-Open Publication No. 2009-192772 obtains illuminating light by synthesizing light from an LED generating red light, an LED generating green light and an LED generating blue light, provides optical sensors for detecting light amounts of the LEDs of the respective colors and controls drive currents supplied to the respective LEDs so as to reduce differences between the light amounts detected by the respective optical sensors and target light amount values. Thus, the apparatus described in Japanese Patent Application Laid-Open Publication No. 2009-192772 makes it possible to obtain illuminating light with a desired color balance.

Note that each LED has a characteristic which differs depending on the color of light generated, and for example, a maximum amount of light emission differs for each color LED. Moreover, the maximum light amount used of each color LED also differs depending on a, color balance setting. That is, an amount of incident light of each optical sensor differs from one color LED to another.

SUMMARY OF THE INVENTION

A light source apparatus according to an aspect of the present invention includes a first light source that emits first light with a first light amount as a maximum light amount used, a second light source that emits second light with a second light amount higher than the first light amount as a maximum light amount used, a first light amount detection section provided on an optical path of the first light and configured to detect a light amount of the incident first light, a second light amount detection section having a detection range identical to a detection range of the first light amount detection section, provided on an optical path of the second light and configured to detect a light amount of the incident second light, a light amount limiting section that limits a light amount of light incident upon the second light amount detection section so that the light amounts detected in the first light amount detection section and the second light amount detection section match a predetermined value within the detection range when light with the first light amount and light with the second light amount are emitted from the first light source and the second light source, and a control section that controls amounts of light emission of the first light source and the second light source based on detection results of the first and second light amount detection sections.

DETAILED DESCRIPTION OF THE PREFERRED EMBODIMENT(S)

Hereinafter, embodiments of the present invention will be described in detail with reference to the accompanying drawings.

(First Embodiment)

Figure 1:
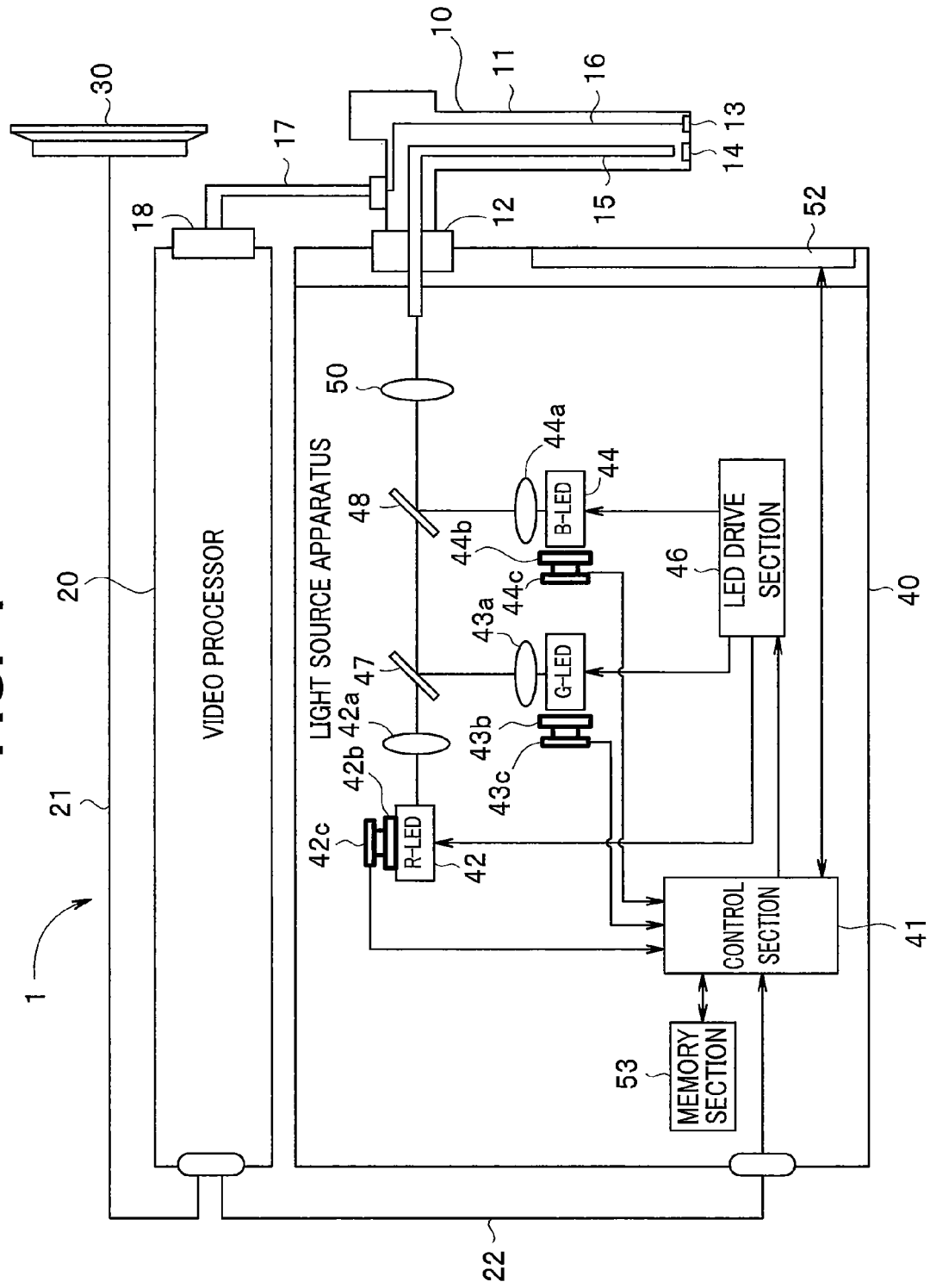
FIG. 1 is a block diagram illustrating a light source apparatus according to a first embodiment of the present invention.

FIG. 1 is a block diagram illustrating a light source apparatus according to a first embodiment of the present invention. The present embodiment is a light source apparatus applied to an endoscope system including an endoscope, a video processor and a monitor.

An endoscope system 1 is constructed of an endoscope 10, a video processor 20, a monitor 30 and a light source apparatus 40. The endoscope 10 includes an elongated insertion portion 11 that can be inserted into inside of a lumen or the like on a distal end side and a proximal end side thereof is detachably connected to the light source apparatus 40 via a connector 12.

The endoscope 10 is detachably connected to the video processor 20 via a cable 17 and a connector 18. Thus, different types of endoscopes can be attached to the light source apparatus 40 and the video processor 20.

An image pickup device 13 configured to pick up a video of an object such as inside of a lumen and a lens 14 configured to irradiate the object with light from the light source apparatus 40 are disposed at a distal end of the insertion portion 11. Through the lens 14, the object is irradiated with illuminating light transmitted from the light source apparatus 40 via a light guide 15. The image pickup device 13 is constructed of a CCD, CMOS sensor or the like, and return light from the object is made incident upon an image pickup surface, the incident optical image of the object is photoelectrically converted and image pickup outputs based on the stored charge are sequentially outputted.

The image pickup device 13 operates in response to a drive signal including a synchronization signal supplied from the video processor 20 and supplies the image pickup output to the video processor 20 via a signal line 16.

The video processor 20 applies predetermined signal processing to the image pickup output and generates a video signal displayable on the monitor 30. The video signal from the video processor 20 is supplied to the monitor 30 via a cable 21. An endoscope image based on the image pickup output can thus be displayed on a display screen of the monitor 30.

Furthermore, the video processor 20 is enabled to control the light source apparatus 40 so that brightness of the picked-up image becomes target brightness. The video processor 20 is configured to output information for adjusting the brightness of the picked-up image to the target brightness to the light source apparatus 40 as brightness control information. The brightness control information is supplied to a control section 41 of the light source apparatus 40 via a cable 22.

The light source apparatus 40 includes an LED (R-LED) 42 that generates red light, an LED (G-LED) 43 that generates green light and an LED (B-LED) 44 that generates blue light. Note that although the present embodiment will describe an example where LEDs for generating light of three colors, the types of color and the number of colors are not limited to those of the present embodiment. In the present embodiment, a plurality of types of LEDs need to be used, and LEDs for generating violet and amber light may be added to FIG. 1, for example.

Lenses 42a to 44a are arranged on optical axes of emitted light of the respective LEDs 42 to 44 respectively. The respective lenses 42a to 44a respectively convert the emitted light of the LEDs 42 to 44 to substantially parallel light and emit the parallel light. Dichroic filters 47 and 48 that make up an optical path section are arranged on an optical axis of the lens 42a which emits light from the R-LED 42. Light from the G-LED 43 is also made incident upon the dichroic filter 47 via the lens 43a. Furthermore, light from the B-LED 44 is also made incident upon the dichroic filter 48 via the lens 44a.

The dichroic filter 47 reflects light from the G-LED 43 and transmits the light from the R-LED 42. The dichroic filter 48 reflects the light from the B-LED 44 and transmits the transmitted light of the dichroic filter 47. In this way, the light of the LEDs 42 to 44 are synthesized by the dichroic filters 47 and 48. The synthesized light from the dichroic filter 48 is designed to enter the light guide 15 via a lens 50. Note that an arrangement order of the LEDs 42 to 44 can be changed by setting characteristics of the dichroic filters 47 and 48 as appropriate, but it is easier to set the characteristics of the dichroic filters if the LEDs 42 to 44 are arranged in the order of wavelength bands of emitted light.

The respective LEDs 42 to 44 are driven and turned on by an LED drive section 46. The LED drive section 46 is controlled by the control section 41 to generate a PWM pulse which is a drive signal for driving each LED. Note that each LED 42 to 44 is designed to emit light with an amount of light emission corresponding to a duty ratio of PWM pulse and a current flow rate from the LED drive section 46. The control section 41 controls the duty ratio of PWM pulse and a current level by outputting light adjustment information for controlling the respective LEDs 42 to 44 to the LED drive section 46, and thereby controls light adjustment of each LED 42 to 44.

The control section 41 generates light adjustment information so that amounts of light emission of the respective LEDs 42 to 44 may maintain a predetermined color balance. The color balance among the respective LEDs 42 to 44 needs to be determined according to spectral sensitivity characteristics of the endoscope 10. A memory section 53 of the light source apparatus 40 stores information on a ratio of light amount to be generated in the respective LEDs 42 to 44 according to spectral sensitivity characteristics of the endoscope 10. The control section 41 is designed to output control information for controlling the respective LEDs 42 to 44 to the LED drive section 46 based on the information on the ratio of light amount stored in the memory section 53.

Note that although the memory section 53 has been described as storing the information on the ratio of light amount of the respective LEDs to obtain an optimum color balance, it is also possible to attach the endoscope 10 to the video processor 20 and the light source apparatus 40, thereby read the information relating to the ratio of light amount from the endoscope 10 and set the information in the control section 41.

However, LEDs have a temperature characteristic and their light amounts change depending on a temperature even when the LEDs have identical current values. Since LEDs have a characteristic that their temperatures rise as the LEDs emit light, the temperature characteristic needs to be taken into consideration to accurately control the amount of illuminating light. Moreover, since a temperature characteristic differs from one color LED to another, a temperature needs to be measured for each LED. However, the LEDs 42 to 44 are arranged relatively close to each other inside the light source apparatus 40 and it is difficult to measure a temperature change by each LED as a single unit. Thus, in the present embodiment, light amounts of the respective LEDs are measured and obtained to thereby control current values.

In this case, an optical sensor with a common dynamic range and having an identical characteristic is used as each optical sensor in the present embodiment. In this case, it is also possible to improve resolution of each optical sensor by controlling the amount of incident light so that the amounts of incident light of light incident upon the respective optical sensors become substantially equal.

Optical sensors 42c to 44c configured to detect the amounts of light from the respective LEDs 42 are disposed in the vicinity of the respective LEDs 42 to 44. The optical sensors 42c to 44c have sufficient sensitivity in wavelength bands of emitted light of the LEDs 42 to 44. The optical sensors 42c to 44c generate output signals proportional to intensities of incident light. Output signals of the optical sensors 42c to 44c are supplied to the control section 41.

In the present embodiment, a light amount limiting member 42b is disposed between the LED 42 and the optical sensor 42c, a light amount limiting member 43b is disposed between the LED 43 and the optical sensor 43c and a light amount limiting member 44b is disposed between the LED 44 and the optical sensor 44c.

The light amount limiting members 42b to 44b are configured to adjust the light amounts of emitted light of the respective LEDs 42 to 44 and enabled to cause the light to enter the optical sensors 42c to 44c. For example, neutral density filters (ND filters) can be adopted as the light amount limiting members 42b to 44b. In the present embodiment, the light amount limiting members 42b to 44b are configured to be able to adjust a ratio of attenuation of light (attenuation factor) in accordance with light-emitting intensities of the LEDs 42 to 44 respectively.

Figure 2:
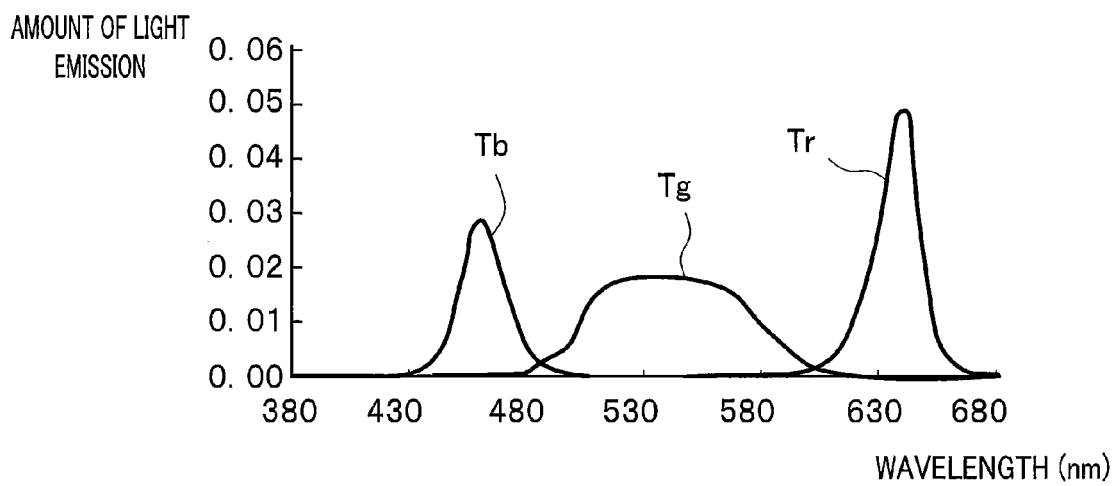
FIG. 2 is a graph illustrating an example of amounts of light emitted from respective LEDs necessary to obtain illuminating light suitable for a predetermined observation mode of an endoscope with a horizontal axis showing a wavelength and a vertical axis showing an amount of light emission.

FIG. 2 is a graph illustrating an example of amounts of light emitted from the respective LEDs necessary to obtain illuminating light suitable for a predetermined observation mode of an endoscope with a horizontal axis showing a wavelength and a vertical axis showing an amount of light emission. Curves Tr, Tg and Tb in FIG. 2 show amounts of light emission necessary for the R-LED 42, the G-LED 43 and the B-LED 44 respectively. As shown in FIG. 2, the amounts of light emission of the respective LEDs necessary to obtain illuminating light suitable for a predetermined observation mode differ from each other.

Figure 3:
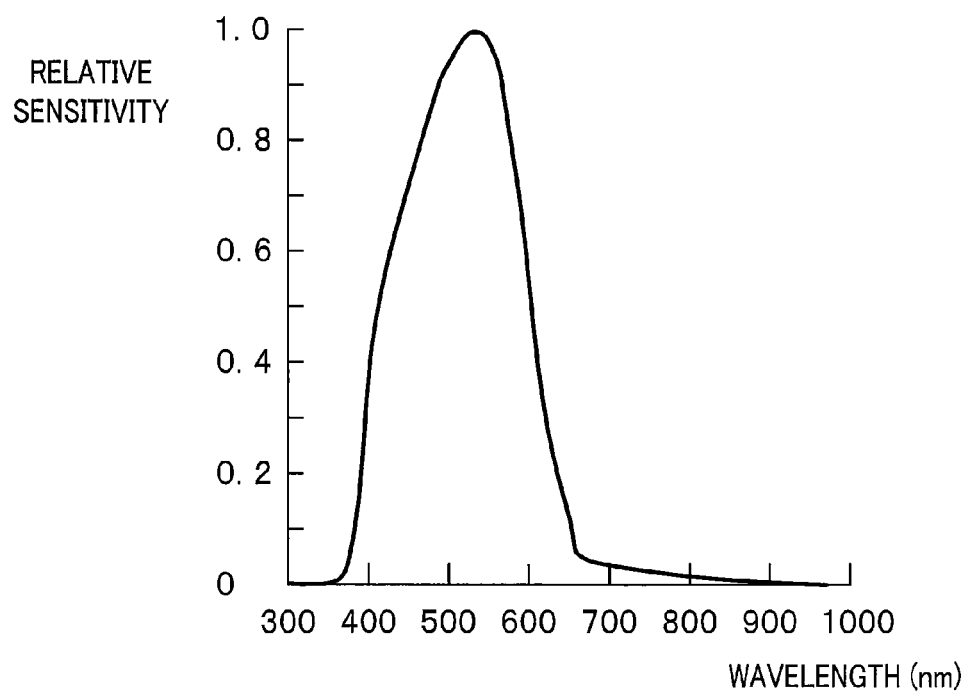
FIG. 3 is a graph illustrating a spectral sensitivity characteristic of optical sensors 42c to 44c with a horizontal axis showing a wavelength and a vertical axis showing relative sensitivity.

FIG. 3 is a graph illustrating a spectral sensitivity characteristic of the optical sensors 42c to 44c with a horizontal axis showing a wavelength and a vertical axis showing relative sensitivity. In the present embodiment, sensors having identical characteristics are adopted for the optical sensors 42c to 44c. A solid line in FIG. 3 shows the spectral sensitivity characteristic.

Figure 4A:
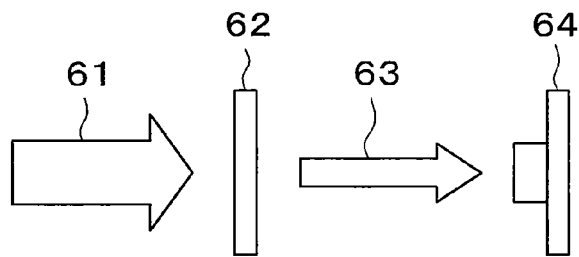
FIG. 4A is a diagram schematically illustrating emitted light from respective LEDs 42 to 44 entering their respective optical sensors 42c to 44c.
Figure 4B:
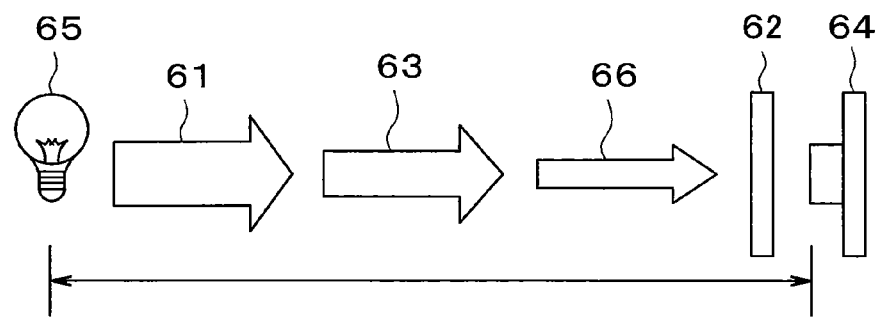
FIG. 4B is a diagram schematically illustrating emitted light from the respective LEDs 42 to 44 entering their respective optical sensors 42c to 44c.

FIG. 4A and FIG. 4B are diagrams schematically illustrating emitted light of the respective LEDs 42 to 44 entering the optical sensors 42c to 44c respectively. Note that in FIG. 4A and FIG. 4B, a light amount limiting member 62 represents the light amount limiting members 42b to 44b and an optical sensor 64 represents the optical sensors 42c to 44c. An arrow 61 at a left end in FIG. 4A represents emitted light beams of the respective LEDs 42 to 44. Each emitted light beam of the LED 42 to 44 is made incident upon the optical sensor 64 corresponding to the optical sensors 42c to 44c via the light amount limiting member 62 corresponding to the light amount limiting members 42b to 44b. A thin arrow 63 on a right side shows that the emitted light of the LEDs 42 to 44 attenuates due to the light amount limiting member 62 and enters the optical sensor 64.

Note that an example has been described in the example of FIG. 1 where the light amount limiting members 42b to 44b and the optical sensors 42c to 44c are arranged in the vicinity of the respective LEDs 42 to 44, but the light amount limiting members 42b to 44b and the optical sensors 42c to 44c can be arranged at any positions other than positions on optical paths from the respective LEDs 42 to 44 to the respective lenses 42a to 44a as appropriate if the optical sensors 42c to 44c can detect amounts of light emission of the respective LEDs 42 to 44.

Furthermore, the amount of light attenuation also changes depending on respective distances between respective LEDs 42 to 44 and respective optical sensors 42c to 44c. FIG. 4B illustrates this condition, and each emitted light of the light source 65 corresponding to the respective LEDs 42 to 44 gradually attenuates as indicated by thicknesses of arrows 61, 63 and 66 and enters the optical sensor 64 corresponding to the optical sensors 42c to 44c via the light amount limiting member 62 corresponding to the light amount limiting members 42b to 44b. The greater the distance from the light source 65 to the optical sensor 64 is, the greater is the amount of attenuation by which light attenuates and enters the optical sensor 64.

Note that the amount of light attenuation also changes depending on the position and the optical axis direction of each LED 42 to 44, the positions of the light amount limiting members 42b to 44b and the optical sensors 42c to 44c and the angle of the incident surface of light, and therefore characteristics of the light amount limiting members 42b to 44b are controlled by setting them to appropriate positions and angles.

In the present embodiment, when light with a maximum light amount used is emitted from each LED 42 to 44, the characteristics (attenuation factor) of the light amount limiting members 42b to 44b is set so that light which has an identical light amount and matches a detection range of each optical sensor 42c to 44c is made incident upon each optical sensor 42c to 44c.

When the optical sensor having the characteristic shown in FIG. 3 is adopted as the optical sensors 42c to 44c, sensitivity of each optical sensor 42c to 44c with respect to each R, G or B light beam is 0.2 for red (R) light and 0.6 for blue (B) light when green (G) light is used as a reference (1).

The ratio of amount of light emission (light emission ratio) among the respective LEDs 42 to 44 suitable for the predetermined observation mode shown in FIG. 3 is assumed to be 0.8:1:0.5 using the amount of light emission of the G-LED 42 as a reference (1). In this case, the ratio of attenuation factor among the respective light amount limiting members 42b to 44b is set so as to be (n÷0.2÷0.8):n:(n÷0.6÷0.5). Table 1 below shows such a relationship of attenuation ratio.

TABLE 1

|  | Light emission color | | |
| --- | --- | --- | --- |
|  | R | G | B |
| Sensor sensitivity ratio | 0.2 | 1 | 0.6 |
| Light emission ratio | 0.8 | 1 | 0.5 |
| Attenuation ratio | n ÷ 0.2 ÷ 0.8 | n | n ÷ 0.6 ÷ 0.5 |

In the example in Table 1, for example, when G light from the G-LED 43 is caused by the light amount limiting member 43b to attenuate to 1/1000, R light may be caused by the light amount limiting member 42b to attenuate by (1/1000)×5×5/4=6.25/1000 and B light may be caused by the light amount limiting member 44b to attenuate by (1/1000)×(5/3)×2=1/300.

The light amount limiting members 42b to 44b having an attenuation ratio corresponding to Table 1 are adopted and the respective LEDs 42 to 44 are thereby caused to emit light with the characteristics in FIG. 2, and even when the optical sensors 42c to 44c of a characteristic identical to that in FIG. 3 are used, light whose maximum amount of incident light of each color light beam corresponds to the detection range is made incident upon each optical sensor 42c to 44c, and it is thereby possible to set resolution available for detection of the amount of incident light to a common and maximum level, and each optical sensor 42c to 44c can detect the amount of light with high accuracy.

In Table 1, characteristics of the respective light amount limiting members 42b to 44b are shown in association with the characteristics in FIG. 2 and FIG. 3, but the characteristics of the respective light amount limiting members 42b to 44b may be set in accordance with the light emission ratio among the respective LEDs 42 to 44 and the sensor sensitivity ratio among the optical sensors 42c to 44c.

Note that the attenuation factor of the light amount limiting member 44b for the B-LED 44 having highest efficiency may generally be set to have a largest value. Furthermore, regarding the characteristics of the optical sensors 42c to 44c, sensitivity with respect to blue (B) light is generally lower than sensitivity with respect to green (G)

light, and therefore characteristics (attenuation factors) of the light amount limiting members 43b and 44b with respect to the G-LED 43 and the B-LED 44 may be consequently set to a comparable level and the characteristic (attenuation factor) of the light amount limiting member 42b with respect to the R-LED 42 may be reduced.

Note that a case has been described in the example in FIG. 1 where the respective optical sensors 42c to 44c are provided with the light amount limiting members 42b to 44b respectively, but it is apparent that a certain degree of effect can be obtained even when light is made incident upon any one or two of the respective optical sensors 42c to 44c via the light amount limiting member.

Thus, according to the present embodiment, light of each LED is made incident upon each optical sensor via each light amount limiting member, a characteristic of each light amount limiting member is individually controlled, and light at an appropriate light amount level can be made incident upon each optical sensor. This makes it possible to make the maximum light amount used of each LED substantially match the detection range of the optical sensor. That is, each optical sensor can obtain the amount of incident light with similar and maximum resolution irrespective of light emission ratio of the LED and characteristic of the optical sensor. It is thereby possible to improve photometric accuracy by each optical sensor and control the light amount ratio of each LED to a color balance optimum to the endoscope connected with high accuracy, for example.

Note that an example of the light source using three light-emitting sections by three LEDs has been described in the above-described embodiment, but it is apparent that the above-described embodiment is applicable to a light source having two or more or four or more light-emitting sections.

(Modifications)

Figure 5:
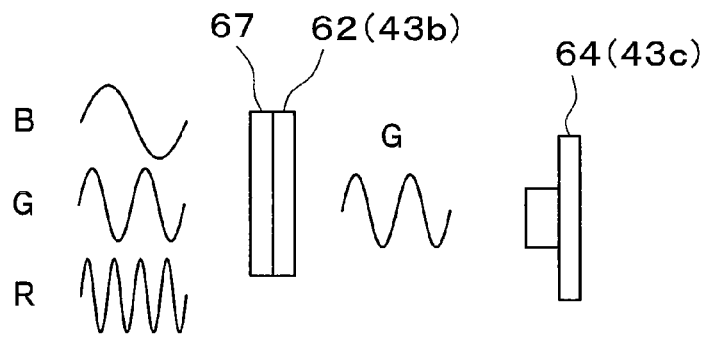
FIG. 5 is a diagram illustrating a modification.
Figure 6:
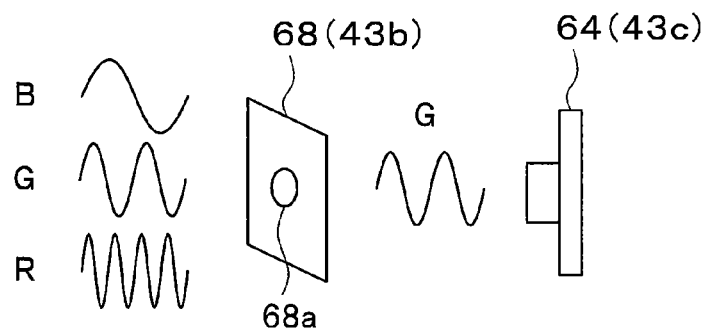
FIG. 6 is a diagram illustrating a modification.
Figure 7:
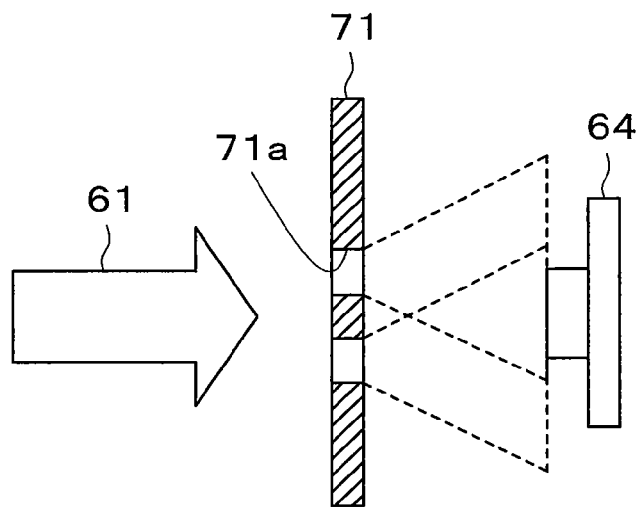
FIG. 7 is a diagram illustrating a modification.

FIG. 5 to FIG. 7 are diagrams illustrating modifications of the present embodiment. The modification in FIG. 5 shows an example where a wavelength cutting filter is used. A wavelength cutting filter 67 and a light amount limiting member 62 are provided between each LED 42 to 44 and each optical sensor 42c to 44c respectively. In the present modification, as shown in FIG. 5, emitted light of each LED 42 to 44 is made incident upon each optical sensor 64 via each wavelength cutting filter 67 and each light amount limiting member 62. Note that FIG. 5 corresponds to G light, and shows an example where the light amount limiting member 62 and the optical sensor 64 are the light amount limiting member 43b and the optical sensor 43c in FIG. 1 respectively.

The wavelength cutting filter 67 provided for each optical sensor 42c to 44c respectively limits a wavelength of light incident upon each optical sensor 42c to 44c and passes only light of a compatible wavelength. That is, the wavelength cutting filter 67 provided in correspondence with the optical sensor 42c passes only the red (R) light and blocks passage of other color light. Similarly, the wavelength cutting filter 67 provided in association with the optical sensor 43c passes only the green (G) light and blocks passage of other color light. Similarly, the wavelength cutting filter 67 provided in association with the optical sensor 44c passes only the blue (B) light and blocks passage of other color light.

When a plurality of LEDs and optical sensors are arranged within a relatively narrow range, leakage light from LEDs other than the LEDs to be inspected may be made incident upon the respective optical sensors. When the respective optical sensors 42c to 44c receive leakage light from LEDs other than the LEDs to be inspected, it is extremely difficult for the respective optical sensors 42c to 44c to accurately detect light amounts of the respective LEDs to be detected.

Thus, in the present modification, the wavelength cutting filter 67 that corresponds to each optical sensor 42c to 44c is provided to prevent leakage light from the LEDs other than the LEDs to be inspected from entering each optical sensor 42c to 44c. In this way, each optical sensor 42c to 44c in the present modification can detect the amounts of light emission of the LEDs to be inspected with high accuracy.

Note that although an example has been described in FIG. 5 where a wavelength cutting filter and a light amount limiting member are combined, the light amount limiting members 42b to 44b themselves may be provided with a wavelength cutting characteristic.

FIG. 6 illustrates an example where a pinhole (diaphragm) member 68 is adopted as the light amount limiting member. Note that FIG. 6 corresponds to G light and shows an example where a pinhole member 68 and an optical sensor 64 correspond to the light amount limiting member 43b and the optical sensor 43c in FIG. 1 respectively. The pinhole member 68 includes an opening section 68a having a predetermined opening diameter. The amount of passing light is limited in accordance with the opening diameter of the opening section 68a. By setting the opening diameter of the pinhole members which is each light amount limiting member 42b to 44b based on the amounts of light emission of the LEDs 42 to 44 and sensitivity characteristics of the optical sensors 42c to 44c as appropriate, it is possible to cause light at levels corresponding to a dynamic range to enter all the optical sensors 42c to 44c and detect amounts of light emission of the respective LEDs 42 to 44 with high accuracy.

Furthermore, FIG. 7 shows another modification and shows an example where a mesh member 71 is adopted as the light amount limiting member. The mesh member 71 includes slits 71a formed at appropriate intervals, and the amount of passing light can be limited by the interval of the slits 71a and a slit size. In this case, effects can be obtained which are similar to those when a pinhole member is adopted.

(Second Embodiment)

Figure 8:
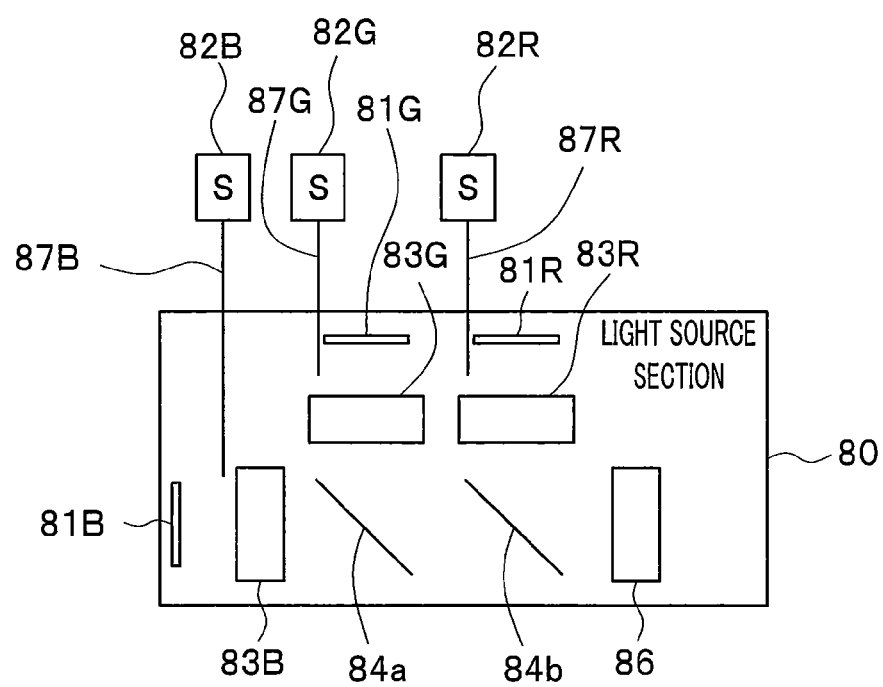
FIG. 8 is a diagram illustrating a second embodiment of the present invention.

FIG. 8 is a diagram illustrating a second embodiment of the present invention. The present embodiment adopts a light guide as the light amount limiting member. Note that FIG. 8 shows only a configuration of an optical system that detects a light amount of each LED of the light source apparatus.

The light source apparatus according to the present embodiment includes a light source section 81 that emits light to an endoscope or the like and three sensors 83R, 83G and 83B. The light source section 81 is provided with three R-LED 81R, G-LED 81G and B-LED 81B that emit R, G and B light beams respectively. Lenses 83R, 83G and 83B are disposed on optical axes of emitted light of the respective LEDs 81R, 81G and 81B respectively. The respective lenses 83R, 83G and 83B respectively convert emitted light of the LEDs 81R, 81G and 81B to substantially parallel light and emit the parallel light. The emitted light beams of the LEDs 81R, 81G and 81B are synthesized by an optical path section made up of dichroic filters 84a and 84b similar to those in the first embodiment. The synthesized light is emitted to an endoscope or the like which is not shown via a lens 86.

In the present embodiment, incident end faces of light guides 87R, 87G and 87B which are light guide members and also light amount limiting members are located in the vicinity of the respective LEDs 81R, 81G and 81B respectively. Emitted light from each LED 81R, 81G, 81B is made incident upon the incident end face of each light guide 87R, 87G or 87B, transmitted through the light guide 87R, 87G or 87B and guided to a light emission end of the light guide 87R, 87G or 87B.

The emission ends of the light guides 87R, 87G and 87B face light receiving surfaces of the respective sensors 82R, 82G and 82B and the sensors 82R, 82G and 82B can detect amounts of light transmitted by the light guides 87R, 87G and 87B. Note that components similar to the optical sensors 42c to 44c in FIG. 1 can be adopted as the sensors 82R, 82G and 82B.

Note that an example has been described in FIG. 8 where the incident end faces of the respective light guides 87R, 87G and 87B are arranged in the vicinity of the LED 81R, 81G and 81B respectively, but the incident end faces of the light guides 87R, 87G and 87B can be arranged at appropriate positions other than the positions on optical paths from the LEDs 81R, 81G and 81B to the respective lenses 83R, 83G and 83B where the sensors 82R, 82G and 82B can receive light allowing the sensors to detect the amounts of light emission from each LED 81R, 81G or 81B.

According to the present embodiment, it is possible to control the amount of attenuation of light transmitted through the light guides 87R, 87G and 87B by changing the number (diameter) of light guides 87 and the length of the light guide 87. By changing at least one of the diameter and the length of the light guide 87R, 87G or 87B in accordance with the amount of light emission of the LED 81R, 81G or 81B and the spectral sensitivity of the sensor 82R, 82G or 82B, it is possible to cause light with substantially the same amount of incident light to enter the sensor 82R, 82G or 82B having identical characteristics. This makes it possible to operate the respective sensors 82R, 82G and 82B at similar resolution and detect the amounts of light emission of the respective LEDs 81R, 81G and 81B with high accuracy.

Note that in the present embodiment, the light guides 87R, 87G and 87B guide emitted light of the LEDs 81R, 81G and 81B to the sensors 82R, 82G and 82B, and therefore, there is an advantage that the sensors 82R, 82G and 82B have a high degree of freedom of arrangement of the sensors 82R, 82G and 82B. For example, the light guides 87R, 87G and 87B can also guide light from the respective LEDs 81R, 81G and 81B to the sensors 82R, 82G and 82B mounted on a substrate which is not shown.

Furthermore, although the present embodiment has been described as using a light guide as an example of the light guide member, the light guide member is not limited to the light guide. For example, the light guide member can be any member that plays the role of transmitting light from an incident end to an emission end such as a rod lens and can adjust the light transmission characteristic in a transmission path.

(Third Embodiment)

Figure 9:
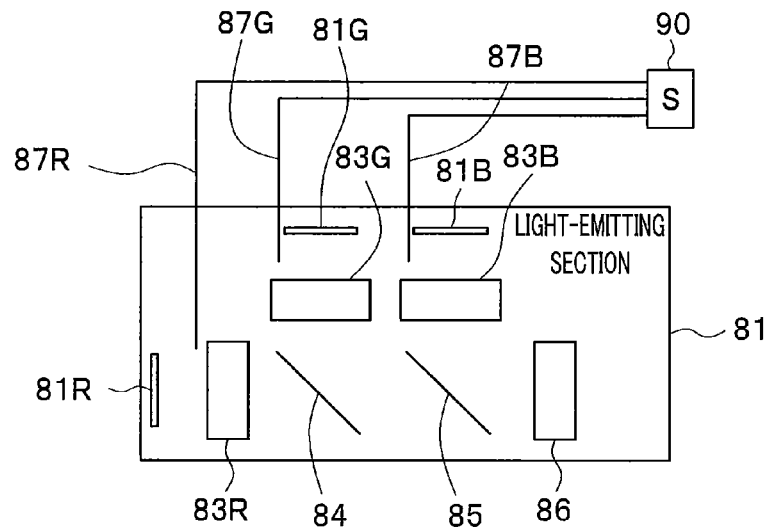
FIG. 9 is a diagram illustrating a third embodiment of the present invention.

FIG. 9 is a diagram illustrating a third embodiment of the present invention. The present embodiment shows an example where a color sensor is used as a sensor. In FIG. 9, the same components as those in FIG. 8 are assigned the same reference numerals and description thereof will be omitted.

The present embodiment is only different from the second embodiment in that one color sensor 90 is adopted instead of the three sensors 82R, 82G and 82B in FIG. 8. For example, a sensor having three light-receiving sections for red, green and blue can be adopted as the color sensor 90, but the sensor is not limited to this.

Respective emission surfaces of the light guides 87R, 87G and 87B that guide emitted light from the LEDs 81R, 81G and 81B face respective incident surfaces of the three light-receiving sections of the color sensor 90. The color sensor 90 is designed to be able to calculate light amounts of R, G and B light incident upon the respective light-receiving sections of R, G and B light.

In the present embodiment, by appropriately setting diameters and lengths of the light guides 87R, 87G and 87B in accordance with amounts of light emission of the LEDs 81R, 81G and 81B and sensitivity characteristics of the R, G and B light-receiving sections of the color sensor 90, it is possible to keep resolution corresponding to R, G and B light of the color sensor 90 at a comparable and maximum level. This allows the color sensor 90 to detect amounts of light emission of the LEDs 81R, 81G and 81B with high accuracy.

Other configurations, operations and effects are similar to those of the second embodiment.

(Fourth Embodiment)

Figure 10:
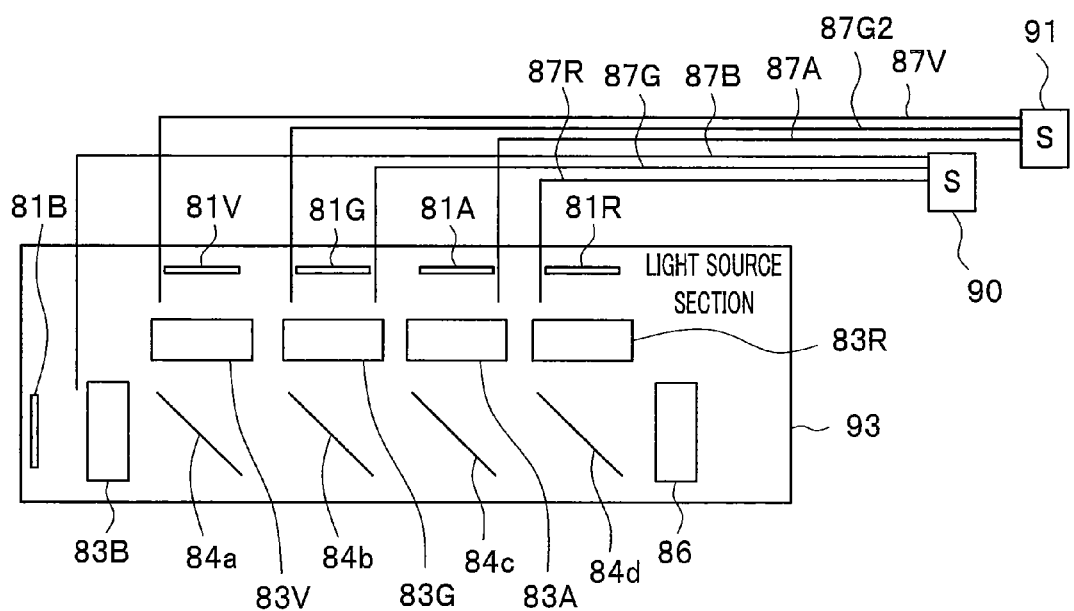
FIG. 10 is a diagram illustrating a fourth embodiment of the present invention.

FIG. 10 is a diagram illustrating a fourth embodiment of the present invention. In FIG. 10, the same components as those in FIG. 9 are assigned the same reference numerals and description thereof will be omitted. The present embodiment shows an example where a color sensor is used as a sensor and LEDs that generate color light of five colors are adopted.

The present embodiment shows an example where the present invention is applied to a light source section 93 including five LEDs 81R, 81G, 81B, 81A and 81V, including an A-LED 81A that emits amber light and a V-LED 81V that emits violet light in addition to the three LEDs 81R, 81G and 81B that emit R, G and B light.

Lenses 83R, 83G, 83B, 83A and 83V are arranged on optical axes of emitted light from the respective LEDs 81R, 81G, 81B, 81A and 81V. The respective lenses 83R, 83G, 83B, 83A and 83V respectively convert emitted light of the LEDs 81R, 81G, 81B, 81A and 81V to substantially parallel light and emit the parallel light. These emitted light beams of the LEDs 81R, 81G, 81B, 81A and 81V are synthesized in an optical path section made up of dichroic filters 84a to 84d. The synthesized light is emitted to an endoscope or the like which is not shown via the lens 86.

In the present embodiment, incident end faces of the light guides 87R, 87G, 87B, 87A and 87V which are light amount limiting members are also located in the vicinity of the respective LEDs 81R, 81G, 81B, 81A and 81V. Furthermore, incident end face of a light guide 87G2 which is a light amount limiting member is also located in the vicinity of the LED 81G in the present embodiment.

Note that in the present embodiment, incident end faces of the light guides 87R, 87G, 87B, 87A, 87V and 87G2 may also be arranged at any positions other than positions on optical paths from the respective LEDs to the respective lenses where it is possible to detect the amounts of light emission of the respective LEDs.

In the present embodiment, emitted light from the five LEDs 81R, 81G, 81B, 81A and 81V are detected by two color sensors 90 and 91. The color sensors 90 and 91 indiscriminately measure violet (V) and blue (B) as blue colors and also indiscriminately detect amber (A) and red (R) as red. Thus, R, G and B light is made incident upon one color sensor 90 via the light guides 87R, 87G and 87B and A, G and V light is made incident upon the other sensor 91 via the light guides 87A, 87G2 and 87V. In this case, the light guides 87G and 87G2 transmit G light of a substantially identical amount of light from the LED 81G. Therefore, it is possible to calculate amounts of light of R, G, B, A and V light emitted by the LEDs 81R, 81G, 81B, 81A and 81V from outputs of the respective sensors using G light incident to the color sensors 90 and 91 as a reference.

The present embodiment also appropriately sets diameters and lengths of the light guides 87R, 87G, 87B, 87A, 87V and 87G2 in accordance with the amounts of light emission of the LEDs 81R, 81G, 81B, 81A and 81V and sensitivity characteristics of the R, G and B light-receiving sections of the color sensors 90 and 91, and can thereby set resolution of the color sensors 90 and 91 for R, G and B light to comparable levels. This allows the color sensors 90 and 91 to detect amounts of light emission of the LEDs 81R, 81G, 81B, 81A and 81V with high accuracy.

In this way, the present embodiment can also obtain effects similar to those of the above-described respective embodiments. Furthermore, according to the present embodiment, it is possible to obtain amounts of light emission of the LEDs of five colors using two color sensors with high accuracy.

Note that the present invention is not limited to the aforementioned respective embodiments as they are, but can also be implemented by modifying the components without departing from the spirit of the invention in the practical stage. Furthermore, various aspects of the invention can be formed using an appropriate combination of a plurality of components disclosed in the above-described respective embodiments. For example, several components may be deleted from all the components shown in the embodiments. Moreover, components applicable to different embodiments may be combined as appropriate.

What is claimed is:

1. A light source apparatus comprising:
a first light source that emits first light at a first light amount as a maximum light amount of the first light source;
a second light source that emits second light at a second light amount as a maximum light amount of the second light source, the second light amount being higher than the first light amount;
a first light amount detection section provided on an optical path of the first light and configured to detect a light amount of the incident first light;
a second light amount detection section having a detection range identical to a detection range of the first light amount detection section, provided on an optical path of the second light, and configured to detect a light amount of the incident second light;
a light amount limiting section that limits a light amount of light incident upon the second light amount detection section based on a position and an optical axis direction of each of the first light source and second light source and on a position and an angle of an incident surface of light of each of the first light amount detection section and the second light amount detection section so that the light amounts detected in the first light amount detection section and the second light amount detection section match a predetermined value within the detection range when light with the first light amount and light with the second light amount are emitted from the first light source and the second light source; and
a control section that controls amounts of light emission of the first light source and the second light source based on detection results of the first and second light amount detection sections,
wherein the light amount limiting section determines an attenuation factor of the amount of light incident upon the second light amount detection section based on a product of a light emission ratio and a sensitivity ratio, the light emission ratio being a ratio between the amount of light emission of the second light source and the amount of light emission of the first light source, the sensitivity ratio being a ratio between a spectral sensitivity of the second light amount detection section and a spectral sensitivity of the first light amount detection section.

2. The light source apparatus according to claim 1,
wherein the light amount limiting section determines an attenuation factor of light based on a relationship between a first light emission ratio which is a ratio of an amount of light emission of the first light source to a reference light amount and a spectral sensitivity characteristic of the first light amount detection section and a relationship between a second light emission ratio which is a ratio of an amount of light emission of the second light source to the reference light amount and a spectral sensitivity characteristic of the second light amount detection section.

3. The light source apparatus according to claim 1,
wherein the light amount limiting section comprises a neutral density filter.

4. The light source apparatus according to claim 3,
wherein the light amount limiting section comprises a wavelength filter that allows the second light amount detection section to pass only light of a color to be detected.

5. The light source apparatus according to claim 2,
wherein the light amount limiting section comprises a slit in which an opening in a size based on the light emission ratio is formed.

6. The light source apparatus according to claim 1,
wherein the light amount limiting section comprises a light guide member that transmits light to be detected to the second light amount detection section, a light transmission characteristic of the light guide member being adjusted so that the light amounts detected in the first light amount detection section and the second light amount detection section match the predetermined value within the detection range when the light of the first light amount and the light of the second light amount are emitted from the first light source and the second light source.

7. The light source apparatus according to claim 6,
wherein the light guide member is a light guide fiber and at least one of a diameter and a length of the light guide fiber is adjusted as the light transmission characteristic.

8. The light source apparatus according to claim 1,
wherein the first and second light amount detection sections comprise color sensors capable of detecting light amounts of a plurality of light beams.

9. The light source apparatus according to claim 1,
wherein the control section controls amounts of light emission of the first light source and the second light source based on detection results of the first light amount detection section and the second light amount detection section, a light amount of which is limited by the light amount limiting section.

* * * * *